(12) United States Patent
Jain (10) Patent No.: US 10,821,200 B2
(45) Date of Patent: Nov. 3, 2020

(54) METHOD OF STERILIZATION OF MICROPARTICLES

(71) Applicant: Hyalo Technologies, LLC, Mendham, NJ (US)

(72) Inventor: Shalabh Jain, Mendham, NJ (US)

(73) Assignee: HYALO TECHNOLOGIES, LLC, Mendham, NJ (US)

( * ) Notice: Subject to any disclaimer, the term of this patent is extended or adjusted under 35 U.S.C. 154(b) by 94 days.

(21) Appl. No.: 15/369,210

(22) Filed: Dec. 5, 2016

(65) Prior Publication Data

US 2018/0154031 A1     Jun. 7, 2018

(51) Int. Cl.
| | |
|---|---|
| *A61L 2/20* | (2006.01) |
| *A61L 2/00* | (2006.01) |
| *A61K 9/19* | (2006.01) |
| *A61K 9/50* | (2006.01) |
| *A61K 9/16* | (2006.01) |

(52) U.S. Cl.
CPC .............. *A61L 2/20* (2013.01); *A61L 2/206* (2013.01); *A61K 9/1647* (2013.01)

(58) Field of Classification Search
CPC ........ A61L 2/206; A61L 2/235; A61L 2/0094; A61L 2/0005; A61K 9/19; A61K 9/50
See application file for complete search history.

(56) References Cited

U.S. PATENT DOCUMENTS

| | | | |
|---|---|---|---|
| 6,149,864 A | 11/2000 | Dillow et al. | |
| 6,395,300 B1 * | 5/2002 | Straub | A61K 9/1611 264/5 |
| 6,716,251 B1 * | 4/2004 | Asius | A61K 8/042 623/23.58 |
| 6,932,983 B1 | 8/2005 | Straub et al. | |
| 8,252,228 B1 | 8/2012 | Freeman et al. | |
| 2003/0078672 A1 | 4/2003 | Shapiro et al. | |
| 2005/0003007 A1 * | 1/2005 | Boix | A61K 9/1647 424/486 |
| 2008/0124400 A1 | 5/2008 | Liggins et al. | |
| 2010/0178344 A1 | 7/2010 | Lambert et al. | |
| 2010/0196486 A1 | 8/2010 | Hiraoka et al. | |

FOREIGN PATENT DOCUMENTS

EP        2985038 A1     2/2016

OTHER PUBLICATIONS

Pinto, Terezinha de Jesus Andreo. "Sterilization: Ethylene Oxide." Encyclopedia of Pharmaceutical Technology (2007) DOI: 10.1081/E-EPT-120012010.*
Ah, Young Chang, et al. "Effects of ethylene oxide gas sterilization on physical properties of poly (L-lactide)—poly (ethylene glycol)—poly (L-lactide) microspheres." Journal of Biomaterials Science, Polymer Edition 12.7 (2001): 783-799.*
Rowe, Raymond C., Paul J. Sheskey, and Siân C. Owen, eds. Handbook of pharmaceutical excipients. Sixth Edition (2009) pp. 117-121.*
Chang, RK, et al. "Aliphatic Polyesters" in Handbook of Pharmaceutical Excipients. Sixth Edition (2009) pp. 23-28.*
Matthews, I.P., C. Gibson, and A.H. Samuel. "Sterilisation of implantable devices." Clinical materials 15.3 (1994): 191-215.*
Mendes, Gisela CC, Teresa RS Brandao, and Cristina LM Silva. "Ethylene oxide sterilization of medical devices: a review." American journal of infection control 35.9 (2007): 574-581.*
Pikal, M.J. "Freeze Drying." Encyclopedia of Pharmaceutical Technology (2007) 1807-1833.*
Nema, S., R.J. Brendel, and R. Washkuhn. "Excipients: Parenteral Dosage Forms and Their Role." Encyclopedia of Pharmaceutical Technology (2007) 1622-1645.*
Burgess, D.J., and A. Hickey. "Microsphere Technology and Applications." Encyclopedia of Pharmaceutical Technology (2007) 2328-2338.*
Petrauskaite, et al., Control of the Porous Structure of Cellulose-Based Tissue . . . , Cellulose Chemistry and Technology, vol. 5, No. 1, pp. 1-19, 2016.
International Search Report issued in PCT Application No. PCT/US2017/062680.
Gurhan Abuhanoglu, A. Yekta Ozer, Radiation Sterilization of New Drug Delivery Systems, Interventional Medicine & Applied Science, vol. 6, No. 2, pp. 51-60, 2014.
Sema Calis, et al., Influence of Irradiation Sterilization . . . , IL Farmaco, vol. 57, pp. 55-62, 2002.
Young Chang AH, et al., Effects of Ethylene Oxide Gas Sterlization . . . , J. Biomater, Sci. Polymer Edn., vol. 12, No. 7, pp. 783-799, 2001.
Yuri V. Il'ichev*, et al., Effects of E-Beam Sterilization on Drug-Eluting . . . , Journal of Chromatographic Science, vol. 49, Nov./Dec. 2011.
K. Viveksarathi, K. Kannan, Effect of the Moist-Heat Sterilization on Fabricated . . . , International Journal of Pharmaceutical Investigation, Apr. 2015, vol. 5, Issue 2.

* cited by examiner

*Primary Examiner* — Bethany P Barham
*Assistant Examiner* — Peter Anthopolos
(74) *Attorney, Agent, or Firm* — Lucas & Mercanti, LLP (57) ABSTRACT

Methods of sterilizing microparticles using a porous solid matrix which allows penetration of a sterilizing gas such as EtO to pass through are disclosed. The methods also include preparing a suspension of the sterilized microparticles by reconstituting the porous matrix containing the microparticles.

31 Claims, 3 Drawing Sheets

METHOD OF STERILIZATION OF MICROPARTICLES

BACKGROUND OF THE INVENTION

Polymer particles of size in the range of few nanometers to several hundred micrometers are of interest as delivery vehicles for pharmaceutical and biotechnology products, as well as therapeutic and cosmetic agents without any medications. Several polymeric microparticles have been approved by the USFDA for use in humans. The particles are known by several names including microparticles, microspheres and nanoparticles. Compositions based on these particles can be formed in a variety of forms including particulate implants, particles included in gels and other topical and non-topical devices, and drug delivery systems. If the particles contain an active medicament, they can serve as long acting delivery devices for therapeutic use. The particles can also be used without an active ingredient incorporated in them. In such a case, the particles act as a medical device. Examples of use of such devices are arterial embolism to kill a tissue or elicit an immune reaction from the body. Other uses of particles as medical devices include their use in skin atrophy and tissue regeneration.

Microparticles can be prepared by using either biodegradable polymers or non-biodegradable polymers. Biodegradable polymers include poly lactic acid, polylactic polyglycolic acid (PLGA) and polyglycolic acid. Non-biodegradable polymers can consist of polystyrene and other similar polymers. Biodegradable polymers are attractive therapeutic and cosmetic systems because they do not have to be removed from the body and do not accumulate over a period of time. They degrade under therapeutic conditions in a time frame that ranges from a few days to several months.

Majority of the microparticle based systems are used by injecting them in the body using a syringe or a similar device. Even when these particles are used in topical applications, they are frequently applied on the skin with wounds. In all of these cases, the microparticles have to be free of living micro-organisms. This included the bacteria, viruses and fungi. Therefore, the microparticles have to be either prepared by using pre-sterilized ingredients by carrying out the entire process under microbe free environment, or have to be sterilized after their preparation.

The process of sterile processing is a cumbersome process and requires special facility and equipment. In addition, sterile processing always leaves a possibility of introducing contamination during the process of manufacturing. Therefore, particle based systems are typically sterilized after the particles have been fabricated.

Several methods of sterilization have been reported for particle based systems. These include the use of heat in the presence or absence of moisture, irradiation of the particles with gamma radiation or electronic beams, use of high intensity plasma, exposure to solvents, and sterilization by gas. An alternative approach will be to carry out the entire process of microparticle production and packaging under sterile conditions.

Use of moist heat to sterilize microparticles involves heating the microparticles to a temperature of 121° C. In the presence of moisture, significant portion of the microparticle forming polymeric material gets hydrolyzed at such a high temperature. Under dry heat sterilization conditions, the required temperatures are considerably higher. Most polymers, especially biodegradable polymers such as PLGA, are susceptible to deformation and/or degradation. Therefore, it is universally accepted that methods based on moist or dry heat are not suitable for sterilization of microparticles for pharmaceutical use.

Gamma irradiation is used to sterilize many PLGA and other microparticles with some success. However, this method involves the use of sophisticated and expensive equipment. In addition, it is reported that gamma radiation may induce degradation of the polymeric materials and result in reduction of molecular weight of the polymer. Calis et. al. (Calis, S., S. Bozdag, K. Suheyla, T. Tuncay and A. A. Hincal, 2002. Influence of Irradiation Sterilization on Poly (lactide-co-glycolide) Microspheres Containing Anti-Inflammatory Drugs. IL Farmaco, 57: 55-62) showed that exposure to gamma radiation at a level typically seen in sterilizations resulted in a significant difference in the particle sizes of the irradiated as compared to the non-irradiated formulations. It was also observed that the rate of active medicament released from PLGA microspheres was higher after irradiation of samples, and this effect was dependent on the dose of the radiation. This results in changes in the release profile of active medicaments in microparticles. Also, use of gamma radiation is typically accompanied by considerable in increase in the product temperature which once again is detrimental to the polymer based microparticles. For this reason, cooling of the samples during irradiation is recommended which adds complexity and cost to the process.

Another potential method of sterilization involving irradiation is the electron beam (E-beam) sterilization. E-beam irradiation is based on the exposure of the sample to high energy electrons under an inert environment. An inert environment is needed to avoid chemical reactions during sterilization. E-beam has been shown by many investigations to lead to several types of chemical reactions in polymer based materials, including microparticles. One such reaction is the formation of cross links between polymer chains. It can also lead to chain-scissioning resulting in the formation of lower molecular weight polymers. In a study by Il'ichev and Alquier (Il'ichev, Yuri and Alquier Lori, Effects of E-BEAM sterilization on drug-eluting stents: paclitaxel degradation elucidated by LC-MS-MS with information dependent acquisition, Journal of Chromatographic Science, Vol. 49, November/December 2011, pp 807-817), it was shown that e-beam sterilization of drug-eluting stents caused degradation results in the formation of numerous degradation products from the active ingredient (paclitaxel) and the polymer (PLGA). Many other studies have shown a similar degrading effect of the e-beam sterilization. This method also requires highly sophisticated and expensive equipment and safeguards.

Use of high intensity plasma has been reported as a method of sterilization of medical devices. This method can be combined with a chemical agent to further increase the efficiency of sterilization. An example of a chemical agent is hydrogen peroxide. However, these methods are suitable only for surface sterilization of materials.

Exposure to non-aqueous solvents has been reported for sterilization of polymeric materials. Typical solvents used include ethyl alcohol. This method is not suitable for most polymer-based microparticles because of the solubility of the polymer in sterilizing solvent. Additionally, the solvent may extract the active ingredient from the microparticles. Hence, this method is not considered suitable for sterilization of microparticles.

Gas sterilization is another method that has been tried for sterilization of microparticles. The most commonly used gas is ethylene oxide (EtO). In this method, the microparticles are exposed to the gas, usually at elevated temperatures until all microbes are killed. This is followed by extensive degassing process to remove all traces of EtO. EtO is a reactive gas and can act as a plasticizer for the polymers. In addition, the methods reported in literature require the use of temperatures in the range of 50-60° C. At this temperature, many polymers, including PLGA, will undergo structural changes. Significant changes in the shape and molecular weight of the polymers has been reported in this method. For example, Ah et. al. (Ah Y C, Choi Y, Kim S Y, Kim S H, Lee K S, Byun Y., Effects of ethylene oxide gas sterilization on physical properties of poly(L-lactide)-poly(ethylene glycol)-poly)L-Lactide) microspheres, J. biomater. Scie. Polym Ed., 2001. Pp 783-799) reported in their study that sterilization of poly lactide-poly ethylene glycol-poly lactide microspheres showed significant and undesirable changes in their degree of crystallinity and shape after sterilization with EtO. Another disadvantage of this method in its current form is that the microparticles may not be completely exposed to the gas, resulting in potential failure of the sterilization process. Therefore, the success of EtO as sterilization process for microparticles has been limited.

SUMMARY OF THE INVENTION

This invention is based on the discovery of compositions that allow full contact of a microparticle based formulation with the sterilizing gas, resulting in a reproducible and successful sterilization of the microspheres. This is accomplished by creating a matrix that allows the suspension of microparticles in a porous solid matrix. The matrix allows easy penetration of the gas, such as EtO. Therefore, all microparticles are readily exposed to the sterilizing effect of the gas.

One aspect of this invention relates to gas sterilization of polymer based microparticles at or close to room temperature to avoid temperature related adverse effects on the microparticles. The matrix, as described in the Detailed Description section, allows a substantially immediate and substantially complete penetration of the gas throughout the matrix composition thereby allowing sterilization to occur at a lower temperature. In accordance with this aspect of the invention, methods of sterilization include:
 a. dispersing microparticles into an aqueous solution having a viscosity of from about 100 to about 4,000 centipoise which contains a viscosity inducing polymer, a stabilizer and, optionally a wetting agent;
 b. lyophilizing the resultant dispersion of step a) to produce a porous polymer matrix upon drying in which the microparticles are substantially dispersed; and
 c. exposing the lyophilized porous polymer matrix containing the microparticles substantially dispersed therein to a sterilizing gas under conditions to sufficient to substantially sterilize the lyophilized porous matrix containing the microparticles substantially dispersed therein.

Another aspect of this invention relates to the formation of a solid matrix with high porosity to aid re-dispersion of microparticles. The ingredients in composition are designed to solubilize or disperse in aqueous solvents rapidly to yield a clear viscous solution that allows a substantially uniform suspension of microparticles.

Another aspect of this invention includes a method of preparation of the matrix that causes the microparticles to be entrapped in the solid porous matrix without significant contact with the other microparticles. This causes the solid matrix to be a substantially uniform mixture of the microparticles and water soluble or water insoluble ingredients.

Yet another aspect of this invention relates to methods of gas sterilization of temperature sensitive microparticles and other pharmaceutical systems by allowing the gas sterilization to be carried out at a lower temperature.

Another aspect of this invention relates to the formulation of the matrix as a suspension that allows easy filling of the microparticle-containing active ingredient dose into final containers in a reproducible manner, followed by removal of the solvent by process such as freeze drying.

Another aspect of this invention is related to the ability to reconstitute the formulation with an aqueous solvent resulting in a suspension where the viscosity of the suspension allows uniform dispersion of microparticles. The reconstitution solvent does not have to contain any additives such as viscosity modifiers because the formulation contains such ingredients.

Advantages of this invention include better stability of the microparticles during and after sterilization due to their immobilization in the matrix, and also improved stability of the suspension after reconstitution with a solvent due to the substantially uniform viscosity of the system.

DETAILED DESCRIPTION OF THE INVENTION

This invention relates to compositions that allow effective sterilization of polymer based microspheres by gas sterilization. The preferred gas for sterilization is ethylene oxide (EtO). Other sterilization gases will be apparent to those of ordinary skill. In some aspects of the invention, the sterilizing is carried out at a temperature of from about 20 to about 50° C.±5° C. In other embodiments, the sterilizing is carried out at temperatures at or below about 37° C. For purposes of the present invention, "conditions sufficient to substantially sterilize" shall be understood to include those conditions, i.e. gas concentration, humidity, and time typically used while carrying out EtO or other suitable gas sterilization at the temperatures described herein.

In a first aspect, there are provided methods of sterilizing microparticles. The methods include:
 a. dispersing microparticles into an aqueous solution having a viscosity of from about 100 to about 4,000 centipoise which contains a viscosity inducing polymer, a stabilizer and, optionally a wetting agent;
 b lyophilizing the resultant dispersion of step a) to produce a porous polymer matrix upon drying in which the microparticles are substantially dispersed; and
 c. exposing the lyophilized porous polymer matrix containing the microparticles substantially dispersed therein to a sterilizing gas under conditions to sufficient to substantially sterilize the lyophilized porous matrix containing the microparticles.

The resulting, sterilized and lyophilized porous matrix containing the microparticles dispersed therein. The microparticles are preferably a solid composition comprising a PLGA based polymer material (i.e. a polylactic co-glycolic acid (PLGA) copolymer which is biodegradable) and a suitable viscosity inducing material, which is preferably a hydrophilic polymer described below.

The PLGA based polymer material refers to microparticles in the size range of 0.05 to 500 micrometer in diameter. The polymer can also be in a different form such as crystals, plates or other shapes as needed for a particular purpose. In micro-particulate form, the usual range of particle diameter is from about 1 micrometer to about 200 micrometer. Preferred range of size based on diameter is about 20-150 micrometer. Although the microparticles used for illustrative purposes herein are based on PLGA polymers, this method is applicable to all temperature sensitive polymers used for making microparticles. While PLGA-based microparticles are preferred, the invention can be carried out using other known particle forming polymers or non-polymeric materials. Some examples of such materials are: polylactones, polyorthocarbonate, polyhydroxybutyrate, polyalkylcyanoacrylates, polyanhydrides, polyorthoesters, polyester, polyamide, polyglycolides (PGA), and co-polymers of gylcolides such as Polylactic glycolic acid (PLGA), glycolide/lactide polymers (PLLA/PGA), polyorthoester, polyacetates, polystyrene, polycarbonates, polysaccharides, polycaprolactone, L-polylactides, block co-polymers of polyesters and linear or star-polyethyleneglycol, poly-beta-hydroxybutyrate, beta-hydroxyvalerate-copolymers, polyaminoacids, hydrophobized hyaluronic acid, dextrans, starches, methyl methacrylate, acrylamide, bisacrylamide, albumin, cellulose, cellulose-based polymers, chitosan, collagen, gelatin, proteins, polyvinyl alcohol (PVA), polyvinylpyrrolidone, polyvinylpyridine, and ethylene glycol polymers. Molecular weights for the polymer can vary somewhat due to the specific polymer and the commercially available molecular weights. It is contemplated that all such commercially available polymers with molecular weight ranges of from a few thousand to 100,000 or higher will be suitable for use herein.

In another embodiment, the microparticles may contain an active medicament which is either dissolved or suspended in the particles. This medicament may be released at a slow rate as the microparticle dissolves or erodes. Examples of such medicaments can include any pharmacological or therapeutic class of drugs. The physical dimensions of the medicaments include, but are not limited to, small molecular weight drugs and high molecular weight drugs such as proteins. The active medicaments may be water soluble or water insoluble. Additional suitable microparticles capable of being sterilized and reconstituted according to the present invention are described in commonly assigned U.S. patent application Ser. No. 14/600,735, the contents of which are incorporated herein by reference.

Suitable viscosity inducing materials are preferably hydrophilic polymers that are soluble or partially soluble in water and impart sufficient viscosity to the solution. Examples of such polymer include cellulose derivatives such as hydroxypropyl cellulose, hydroxypropyl methyl cellulose, carboxymethyl cellulose, and hydroxyethyl cellulose. Alternatives include alginic acid and its derivatives, carrageenan, and polyethylene glycol. These polymers may also be used as their salts, for example, carboxymethyl cellulose may be used as the sodium salt. One preferred polymer used in this invention is sodium carboxymethyl cellulose (referred to herein as Na CMC or CMC). Other viscosity inducing materials with similar properties may also be suitable. It is this viscosity inducing material or polymer which forms the matrix which supports the microparticles after lyophilization of the dispersion containing the viscosity inducing polymer, stabilizer and optional wetting agent and microparticles. Thus, the viscosity inducing polymer is used synonymously herein with the term "matrix forming polymer".

In one embodiment, the aqueous dispersions containing the polymer, stabilizer and optional wetting agent also includes the microparticles at a concentration of from about 10 to about 500 mg per milliliter of the dispersion prior to lyophilization. In alternative embodiments, the concentration of the particles is from about 10 to about 200 mg per milliliter of the dispersion. This generally corresponds to a polymer concentration of from about 0.1 to 2 percent on weight by volume basis in water.

Aqueous solutions containing the polymer concentrations in this range can have a viscosity in the range of from about 100 to about 4000 centipoise and in alternative aspects, from about 100 to about 2,000.

The polymer matrix-based compositions in this invention makes it possible to use EtO sterilization at a temperature of about 50° C. or less by causing the microparticles to be suspended in a porous matrix of another polymer such as carboxymethyl cellulose, hydropropylmethyl cellulose, hydroxypropyl cellulose, hydroxyethyl cellulose, alginic acid and its derivatives, carrageenan, and polyethylene glycol.

The composition in this invention is in the solid state in which the microparticles are substantially uniformly dispersed in a solid matrix. The matrix, composed substantially of a hydrophilic polymer can be prepared by suspending the microparticles in a dispersion of the matrix forming polymer, stabilizer, and optional wetting agent, along with other optional ingredients if desired, followed by removal of the solvent. The most common way of solvent removal will be by freeze drying or lyophilizing the suspension.

This process will selectively remove the solvent, leaving behind an undisturbed solid matrix which contains the matrix forming polymer in which the microparticles are substantially uniformly suspended. Removal of the solvent results in formation of pores throughout the matrix which makes it possible for the sterilizing gas to penetrate all areas of the composition.

The aqueous dispersion containing the microparticles and viscosity inducing polymer will also include a stabilizer such as other polymers or small molecules may be added to protect microparticles during the process of freezing and drying. Examples of small molecules include polyhydric sugars such as sucrose, mannitol, and trehalose. Glycine or other cryo-preservatives and lyo-preservatives known to persons skilled in art can be included as well if desired. In many embodiments, the preferred stabilizer is mannitol. The stabilizer will be included in the aqueous dispersion prior to lyophilization at a concentration range of 5-15% w/v.

The aqueous dispersion also optionally includes a wetting agent such as an ionic or non-ionic surfactant, which aids in forming a substantially uniform suspension of particles by improving wetting of particles by the solvent. These surfactants can be non-polymeric small molecules or polymeric in nature. Examples of some preferred polymeric surfactants are polyvinyl pyrrolidone (PVP) and polyvinyl alcohol (PVA). The amount of wetting agent included in the dispersion can range from about 0.1 to about 0.3 wt %. In some alternative aspects the wetting agents include polyethylene glycol, Tween 20 and Tween 80. The wetting agent is preferably included as part of the aqueous dispersion and thus the subsequent protective matrix made therefrom when the sterilization is carried out at temperatures of greater than about 45° C. and more preferably when the sterilization is carried out at temperatures of about 50° C. or higher.

The pH of the aqueous solution prior to the addition of particles is usually between about 4.0 to about 8.0 and is preferably from about 6.0 to about 7.5.

Some preferred aqueous solutions included in the present invention include
  i) from about 0.1 to about 2.0%/wt water soluble, viscosity inducing polymer;
  ii) from about 5 to about 15%/wt stabilizer; and optionally
  iii) from about 0.1 to about 0.3%/wt wetting agent, with the water soluble viscosity inducing polymer preferably being NaCMC, the stabilizer preferably being mannitol; and the wetting agent preferably being polyvinylpyrrolidone (PVP). It is to this aqueous solution that the microparticles are added, thereby forming the dispersion which is eventually lyophilized, sterilized and then reconstituted upon need.

The protective polymer matrix of the invention can be produced by adding the viscosity inducing polymer, stabilizer and, where appropriate, the wetting agent to a suitable solvent which is preferably water but can alternatively be partially or completely a non-aqueous solvent. This is followed by dissolving all the ingredients with the aid of stirring and/or heating. Once a clear solution is obtained, the microparticles are added and the composition is stirred to obtain a substantially uniform suspension of particles. This suspension is frozen using a suitable process such as storage in a −80° C. freezer or by exposing to dry ice (solid carbon dioxide) or liquid nitrogen.

The composition can also be frozen to below −40° C. by placing on a platform that is cooled to below −40° C. Once the composition is frozen, it is dried under a very high vacuum (low pressure) to allow all the solvent to evaporate from solid state to vapor state. This process, known as lyophilization or freeze drying results in a porous cake which is essentially devoid of any solvent. This leaves the composition as a solid porous cake comprising of a uniform suspension of microparticles in a solid matrix. This matrix is stable at room temperature and can be subject to sterilization by a variety of techniques, including gas sterilization.

A person skilled in art will understand that a suitable porous solid matrix can be prepared by using a variety of other ingredients such as polyvinyl alcohol, other cellulose and non-cellulose based polymers and proteins. A suitable matrix can also be obtained by using a crosslinked protein or polymer composition. Such aspects are within the scope of the invention. Regardless of the polymer or substance used to make the matrix, it is creation of a matrix of a polymeric or non-polymeric substance that affords uniform dispersion of microparticles and provides protection of from effects of low and high temperature. It is also clear that while in most aspects of the invention, the gas sterilization can be preferably carried out at temperatures from about room temperature to about 50° C., the sterilization can also be done at temperatures outside this range, if desired without undue experimentation.

In accordance with another aspect of the invention, there are provided methods of reconstituting the sterilized, lyophilized porous matrix containing the microparticles. These methods include contacting the sterilized, lyophilized porous matrix containing the microparticles with an amount of a reconstitution solvent sufficient to substantially resuspend the microparticles within the matrix. The reconstitution solvent is preferably water or an aqueous-based liquid.

Example 1

Preparation of Large Microparticles:

One gram of polylactic co-glycolic acid polymer (50:50), average molecular weight of about 30,000 Daltons, was dissolved in 9 milliliters of dichloromethane. This solution was added to a syringe and a syringe pump was used to cause the solution to flow through a tube with an internal diameter of 2 millimeter. The other end of the tube was in touch with a 3 mm diameter sonication tip that was attached to a frequency generator and an amplifier. A vessel filled with 1000 milliliters of a hardening solution containing 1% polyvinyl alcohol in water was placed below the sonication tip or device to receive the droplets. The process of particle production was started by switching the sonication device on to produce sonication energy and starting the syringe pump set to deliver the particle forming solution at a rate of 6 milliliters per minute. The amplitude of the device was set and maintained throughout the process at 20% at a fixed frequency of 20,000 kilohertz. The droplets formed from the sonication tip were collected in the vessel containing the hardening solution which was being constantly stirred with an overhead stirrer. This process was continued until all the particle forming solution was delivered by the syringe pump.

The hardening solution containing the droplets of particle forming solution was constantly stirred for a period of 8 hours after which the particles are allowed to settle. The particles were recovered from their suspension by filtration through a filter of less than 5 micrometer pore size. The particles were repeatedly washed with distilled water, resuspended in a small amount of water and frozen at −40 degree Celsius. The particles were subsequently lyophilized to obtain solid particles. The particle size as measured by microscopy is in the range of 60-200 microns with 80% of the particles being in the range of 90-160 microns, RSD of less than 30%. The particles from this example were passed through sieves of appropriate size to obtain lots containing particles of average diameter of 130 micrometers and 70 micrometers.

Example 2

Preparation of Small Microparticles:

One gram of polylactic co-glycolic acid polymer (50:50), average molecular weight of about 30,000 Daltons, was dissolved in 9 milliliters of dichloromethane. This solution was added to 50 milliliters of a 2% w/v solution of polyvinyl alcohol (PVA) in water in a 250 mL beaker. The suspension was stirred at a high rate using a magnetic stirring bar for 4 hours. Hardened particles were recovered from the suspension by centrifugation of the suspension at 3000 rpm for several minutes. The particles were washed repeatedly with 5 milliliters of water, transferred to a suitable vial, frozen at −40° C. and freeze dried overnight to obtain a powder. The size range of the particles was 2-40 micrometers with average size being 10 micrometers.

Example 3

Preparation of Material for Sterilization by Bulk Freeze Drying

For each composition listed in Table 1 below, 50 mL of deionized water was added to a 250 mL size beaker along with a magnetic stirring bar. While the liquid was being stirred, appropriate amounts of polymer, e.g. sodium carboxymethyl cellulose, or hydroxylpropylmethyl cellulose (HPMC), wetting agent, e.g. PVP, or PVA, and stabilizer, e.g. mannitol or sucrose, were added as indicated in Table 1. All the solutions did not contain all ingredients as explained in Table 1. The solution was stirred rapidly until a clear solution was obtained. To this solution, 6 grams of particles of the size as indicated in Table 1 were added, resulting in a suspension containing 100 milligrams of particles per milliliter of suspension for compositions 1-3, 5, 6 and 8-42. In compositions 4 and 7, however, 12 grams of particles were added to have the final concentration of particles at 200 milligrams per milliliter of suspension. The mixture was stirred to obtain a uniform suspension. Enough water was added to the beaker to bring the total volume to 60 milliliters. The mixture was stirred for additional few minutes to obtain a uniform suspension of particles in the matrix forming solution.

TABLE 1

Microparticle matrix compositions

| Composition # | Polymer | Polymer, Conc. % w/v | PVP % w/v | Mannitol % w/v | Glycine % w/v | Sucrose % w/v | Particles % w/v | Particle diameter micrometers |
|---|---|---|---|---|---|---|---|---|
| 1 | Sod. CMC | 1 | 0.2 | 15 | 0 | 0 | 10 | 130 |
| 2 | Sod. CMC | 1 | 0.2 | 5 | 0 | 0 | 10 | 130 |
| 3 | Sod. CMC | 1 | 0.2 | 0 | 0 | 0 | 10 | 130 |
| 4 | Sod. CMC | 1 | 0.2 | 15 | 0 | 0 | 20 | 130 |
| 5 | Sod. CMC | 0.5 | 0.2 | 15 | 0 | 0 | 10 | 130 |
| 6 | Sod. CMC | 1 | 0.2 | 15 | 0 | 0 | 10 | 70 |
| 7 | Sod. CMC | 1 | 0.2 | 15 | 0 | 0 | 20 | 70 |
| 8 | Sod. CMC | 0.5 | 0.2 | 0 | 0 | 0 | 10 | 130 |
| 9 | Sod. CMC | 0.5 | 0 | 0 | 0 | 0 | 10 | 130 |
| 10 | Sod. CMC | 0 | 0.2 | 15 | 0 | 0 | 10 | 130 |
| 11 | Sod. CMC | 0 | 0 | 15 | 0 | 0 | 10 | 130 |
| 12 | Sod. CMC | 0 | 0 | 0 | 0 | 0 | 10 | 130 |
| 13 | Sod. CMC | 1 | 0 | 15 | 0 | 0 | 10 | 130 |
| 14 | Sod. CMC | 0.1 | 0.2 | 0 | 0 | 0 | 10 | 130 |
| 15 | Sod. CMC | 0.1 | 0.2 | 15 | 0 | 0 | 10 | 130 |
| 16 | Sod. CMC | 0.1 | 0.2 | 5 | 0 | 0 | 10 | 130 |
| 17 | Sod. CMC | 0.1 | 0 | 15 | 0 | 0 | 10 | 130 |
| 18 | Sod. CMC | 0.05 | 0 | 5 | 0 | 0 | 10 | 130 |
| 19 | Sod. CMC | 0.05 | 0.2 | 5 | 0 | 0 | 10 | 130 |
| 20 | Sod. CMC | 0 | 0 | 0 | 10 | 0 | 10 | 130 |
| 21 | Sod. CMC | 0 | 0 | 0 | 0 | 1 | 10 | 130 |
| 22 | Sod. CMC | 0 | 0.2 | 0 | 1 | 0 | 10 | 130 |
| 23 | Sod. CMC | 0 | 5 | 0 | 10 | 0 | 10 | 130 |
| 24 | Sod. CMC | 0 | 0.2 | 0 | 0 | 1 | 10 | 130 |
| 25 | Sod. CMC | 0 | 5 | 0 | 0 | 10 | 10 | 130 |
| 26 | Sod. CMC | 0 | 0.2 | 0 | 0 | 0 | 10 | 10 |
| 27 | Sod. CMC | 0 | 5 | 0 | 0 | 0 | 10 | 10 |
| 28 | Sod. CMC | 0 | 0.2 | 0 | 0 | 1 | 10 | 10 |
| 29 | Sod. CMC | 0 | 5 | 0 | 0 | 10 | 10 | 10 |
| 30 | Carbomer | 0.5 | 0 | 15 | 0 | 0 | 10 | 130 |
| 31 | Carbomer | 0.5 | 0 | 5 | 0 | 0 | 10 | 130 |
| 32 | Carbomer | 0.5 | 0 | 0 | 0 | 0 | 10 | 130 |
| 33 | Carbomer | 0.05 | 0 | 15 | 0 | 0 | 10 | 130 |
| 34 | Carbomer | 0.05 | 0 | 5 | 0 | 0 | 10 | 130 |
| 35 | Carbomer | 0.05 | 0 | 0 | 0 | 0 | 10 | 130 |
| 36 | HPMC | 2 | 0 | 15 | 0 | 0 | 10 | 130 |
| 37 | HPMC | 2 | 0 | 5 | 0 | 0 | 10 | 130 |
| 38 | HPMC | 2 | 0 | 0 | 0 | 0 | 10 | 130 |
| 39 | HPMC | 0.2 | 0 | 15 | 0 | 0 | 10 | 130 |
| 40 | HPMC | 0.2 | 0 | 5 | 0 | 0 | 10 | 130 |
| 41 | HPMC | 0.2 | 0 | 0 | 0 | 0 | 10 | 130 |
| 42 | HPMC | 2 | 0 | 0 | 0 | 15 | 10 | 130 |

Each of the above suspensions was added to a glass petri dish with a diameter of 5 inches to increase the surface area. The dish was placed in the freeze dryer and cooled to a temperature of −40° C. for 2 hours. The material was subject to freeze drying by applying a vacuum of less than 200 millitorrs for 24 hours while the temperature of the dish was allowed to rise to 0° C. Following this initial phase of drying, the temperature of the dish was increased to 25° C. and vacuum continued for another 2 hours. The dish was then removed from the freeze dryer and the material was removed with a spatula and mixed to obtain a uniform solid material. An amount of this material containing 100 mg particles was weighed in 10 ml vials for sterilization.

Example 4

Preparation of Material for Sterilization by Vial Freeze Drying

For all compositions 1-42 in Table 1, the particle suspension was prepared as described in the first paragraph of Example 3.

The above suspension was divided in 10 mL vials by adding 1 mL of the suspension in each vial. This suspension was frozen to a temperature of −40° C. in a freezer or on shelf of a freeze dryer. The material was subject to freeze drying by applying a vacuum of less than 200 millitorrs for 24 hours while the temperature of the dish was allowed to rise to 0° C. after one hour of vacuum application. Following this initial phase of drying, the temperature of the dish was increased to 25° C. and vacuum continued for another 2 hours. The vials were removed and packaged for sterilization.

Example 5

Sterilization by Ethylene Oxide

The vials containing freeze dried matrix compositions were placed in a tray. The tray was placed inside a gas sterilization pouch that was large enough to completely wrap and seal the tray. The tray containing the vials in the sterilization pouch was placed in ethylene oxide sterilizer. The vials were subjected to two different cycles of sterilization. These cycles varied in temperature. In one cycle, the temperature during sterilization was maintained at 37° C., while in the second cycle, the temperature was maintained at 50° C. Following completion of the sterilization cycle, the vials were removed from the sterilization chamber and stored at room temperature for 24 hours to allow the gas to dissipate completely.

The vials were removed from the pouches in a sterile laminar flow hood. The vials were capped using rubber stoppers that were pre-sterilized with steam. This procedure was carried out under aseptic conditions. The stoppered vials were then sealed with an aluminum seal. As a control, microparticles which were not placed in a protective polymeric matrix were also subjected to the same sterilization process. See Figures 1 and 2.

Example 6

Testing for Acceptability after Reconstitution

One or two vials of each composition in Table 1 were reconstituted as a suspension by adding 1 milliliter of purified water to each vial using a syringe and a needle. The vials were gently shaken and inverted a few times. The resulting suspension was observed for uniformity of dispersion. The samples were removed and observed under a light microscope to look for physical changes in the particle morphology. The results of the physical observations of dispersion are listed in Table 2. Compositions that allowed a uniform suspension without substantial change in particle morphology were rated as acceptable as indicated by yes notation in Table 2. Compositions that did not allow the formation of a uniform suspension or showed substantial changes in particle morphology were rated as not acceptable as indicated by no notation in Table 2.

TABLE 2

| Composition # | Volume of dried cake % of suspension volume | Reconstitution after EtO sterilization at 37 C. Acceptability | Reconstitution after EtO sterilization at 50 C. Acceptability | Viscosity Centipoise |
|---|---|---|---|---|
| 1 | 100 | yes | yes | 2000 |
| 2 | 90 | yes | yes | 2000 |
| 3 | 60 | no | no | 2000 |
| 4 | 100 | yes | yes | 2000 |
| 5 | 90 | yes | yes | 1000 |
| 6 | 90 | yes | yes | 2000 |
| 7 | 100 | yes | yes | 2000 |
| 8 | 40 | no | no | 1000 |
| 9 | 30 | no | no | 1000 |
| 10 | 90 | no | no | less than 10 |
| 11 | 90 | no | no | less than 10 |
| 12 | 10 | no | no | less than 10 |
| 13 | 100 | yes | no | 2000 |
| 14 | 70 | no | no | 100 |
| 15 | 80 | yes | no | 100 |
| 16 | 50 | no | no | 100 |
| 17 | 80 | no | no | 100 |
| 18 | 40 | no | no | 50 |
| 19 | 40 | no | no | 50 |
| 20 | 50 | no | no | less than 10 |
| 21 | 10 | no | no | less than 10 |
| 22 | 10 | no | no | less than 10 |
| 23 | 50 | no | no | less than 10 |
| 24 | 10 | no | no | less than 10 |
| 25 | 50 | no | no | less than 10 |
| 26 | 5 | no | no | less than 10 |
| 27 | 5 | no | no | less than 10 |
| 28 | 10 | no | no | less than 10 |
| 29 | 50 | no | no | less than 10 |
| 30 | 60 | no | no | more than 10,000 |
| 31 | 60 | no | no | more than 10,000 |
| 32 | 60 | no | no | more than 10,000 |
| 33 | 60 | no | no | more than 5,000 |
| 34 | 60 | no | no | more than 5,000 |
| 35 | 60 | no | no | more than 5,000 |
| 36 | 90 | yes | no | 100 |
| 37 | 90 | yes | no | 100 |
| 38 | 90 | no | no | 100 |
| 39 | 80 | no | no | 10 |
| 40 | 80 | no | no | 10 |
| 41 | 80 | no | no | 10 |
| 42 | 90 | yes | no | 100 |

As shown in Table 2, several compositions for the matrix were not only successfully sterilized at or above 37° C. but were also successfully reconstituted thereafter. CMC concentration of 0.5 to 1.0% on w/v basis in the solution before addition of particles prior to sterilization has been shown to work when other protectants such as mannitol are also present in concentration range of 5-15% on w/v basis in the same solution. When CMC was used alone, it was not able to provide a matrix that could allow both successful sterilization and a resulting in a solid cake that can be reconstituted into a uniform suspension by addition of an aqueous solution. In some compositions a different polymer called hydroxypropylmethyl cellulose (HPMC) was used in the concentration range of 0.2 to 2% on w/v basis in solution prior to the addition of particles. In these compositions, the 2% concentration of HPMC resulted in successful sterilization at 37° C. and 50° C. in the presence of 15% w/v mannitol but only at 37° C. in the presence of 5% w/v mannitol. When 15% w/v sucrose was used as the small molecule stabilizer, the composition containing 2% w/v HPMC was only successful at 37° C. but not at 50° C. This shows that while more than one stabilizers can be used, not all stabilizers work to the same degree of success.

Even when the concentration of particles was doubled from 100 to 200 mg/ml, success was achieved. For example, in composition 4, 200 mg/ml of particles with an average diameter of 130 micrometers were used in a pre-lyophilization dispersion containing CMC, mannitol and PVP in a concentration of 1.0, 15 and 0.2 percent on w/v basis, respectively. This system was successfully sterilized at both 37° C. and 50° C. by EtO and then reconstituted. The same concentrations of CMC and mannitol were also successfully sterilized and re-constituted using a suspension containing 200 mg/ml of microparticles of average diameter of 70 micrometers, as shown in composition 7 in Table 1 and results in Table 2.

In compositions 10-12, viscosity inducing polymer was not added. However, stabilizer and wetting agent were added in different proportions as indicated in Table 1. None of these compositions resulted in product that could be successfully reconstituted after EtO sterilization at 37° C. or 50° C. It is to be noted that in compositions 10 and 11, the volume of the dry cake was about 90% of the volume of suspension prior to freeze drying. This shows that viscosity inducing polymer is needed to obtain a uniform suspension of particles.

In compositions 20-29, viscosity inducing polymer was not added. In these compositions, additional amounts of PVP and some cases other small molecule stabilizers such as glycine and sucrose were added in various concentrations as shown in Table 1. None of these compositions resulted in product that could be successfully reconstituted after EtO sterilization at 37° C. or 50° C. In all of these compositions, the volume of the final cake after freeze drying was 50% or less than 50% of the volume of suspension prior to freeze drying.

As can be seen from results in Table 2, the viscosity of the solution prior to the addition of particles is an important parameter. For example, compositions 15 has a viscosity of about 100 centipoise but does not result in successful sterilization at 37° C. or 50° C. because it does not have a stabilizer. However, the composition 15 with the same viscosity of the solution but with 15% concentration of a stabilizer results in successful sterilization at 37° C. but not at 50° C. When the concentration of the stabilizer is reduced to 5% w/v as shown in composition 16, sterilization is not successful at 37° C. or 50° C. Since the viscosity of the matrix forming solution prior to the addition of particles is about 100 centipoise in compositions 14-16, role of the level of the stabilizer is noted when the viscosity of the solution is relatively low. However, as seen in compositions 1 and 2 in Table 2, both 5% and 10% w/v concentration of the stabilizer result in successful sterilization at 37° C. or 50° C. because the viscosity of the solution prior to the addition of particles is about 2000 centipoise. In composition 3, where the viscosity of the solution prior to the addition of particles is also about 2000 centipoise, the sterilization is unsuccessful at both 37° C. or 50° C. because the stabilizer is not present in this composition. Based on these observations, it is clear that a minimum viscosity of about 100 centipoise if needed for successful sterilization at both temperatures. When the viscosity of the matrix forming solution prior to the addition of particles is less than about 2000 centipoise, the level of the stabilizer also has an effect on success of sterilization.

It is also to be noted that all compositions sterilized at either or both temperature conditions of 37° C. or 50° C. and which resulted in successful re-suspension had a high porosity value. The porosity is the void space in the matrix and is estimated from the volume of the dried cake after lyophilization relative to the volume of the suspension prior to lyophilization. This property is expressed as percent volume of the dried cake relative to the volume of the suspension prior to lyophilization as shown in Table 2. When there is no change in the volume of the cake relative to the volume of the suspension, this percent value is 100. As seen in Table 2, all compositions with successful sterilization at one or both temperature conditions have two things in common; they contain enough viscosity inducing polymer to have a viscosity of higher than about 100 centipoise and their cake volume is higher than about 80% of the suspension volume. This is clear from composition 11 where the dried cake volume is 90% of the suspension volume but sterilization is not successful under either temperature conditions because the there is no viscosity inducing polymer.

In some compositions, no wetting agents such as PVP was added to the solution prior to the addition of particles. In such cases, the sterilization was successful when carried out at the lower temperature of 37° C. but not when carried out at the higher temperature of 50° C. As shown in example 36, the sterilization is successful at 37° C. but not successful at 50° C. Similar results are observed in composition 13 where the wetting agent is not added. However, in composition 1, where the wetting agent is added, sterilization is successful at both 37° C. and 50° C. The only difference between compositions 1 and 13 is that composition 1 contains a wetting agent and composition 13 does not contain a wetting agent. These results suggest that a wetting agent is beneficial when sterilization is carried out at the higher temperature.

Figure 1:
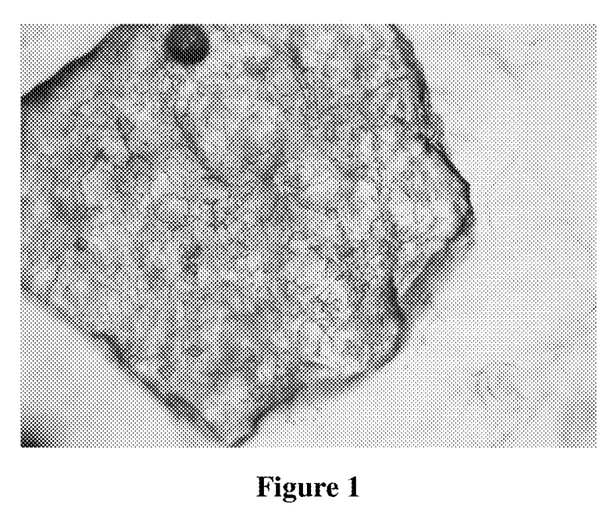
FIG. 1 shows light microscopic picture of large particles without any matrix after EtO sterilization at 50° C.
Figure 2:
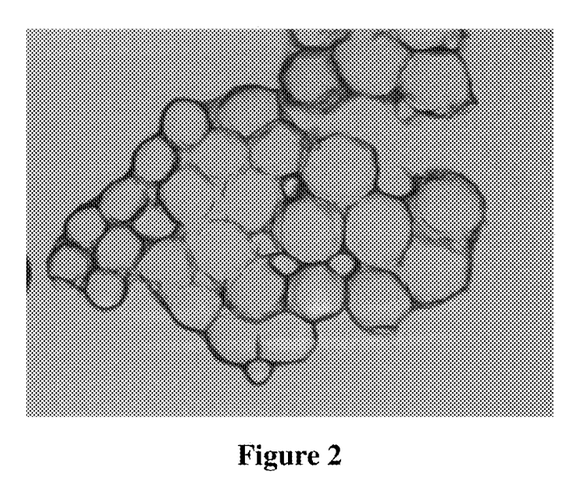
FIG. 2 shows light microscopic picture of large particles without any matrix after EtO sterilization at 37° C.

As shown in FIGS. 1 and 2, when particles without any additives are sterilized using EtO at 50° C. or 37° C. respectively, they melt, fuse together and are destroyed. These particles cannot be reconstituted as a suspension after sterilization. This data shows that the particles by themselves do not withstand EtO sterilization at 37° C. or 50° C. as evidenced by formation of clumps and insoluble material in the reconstituted suspension. Furthermore, when observed under the microscope, the particles appear deformed and fused together.

Figure 3:
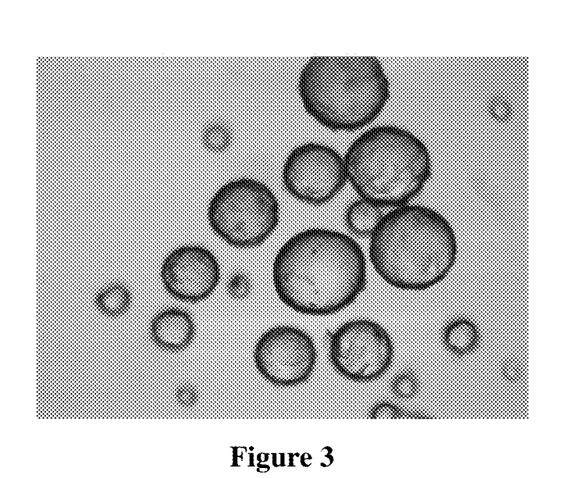
FIG. 3 shows light microscopic picture of large particles after EtO sterilization at 37° C. in matrix according to composition 1 in Table 1.
Figure 4:
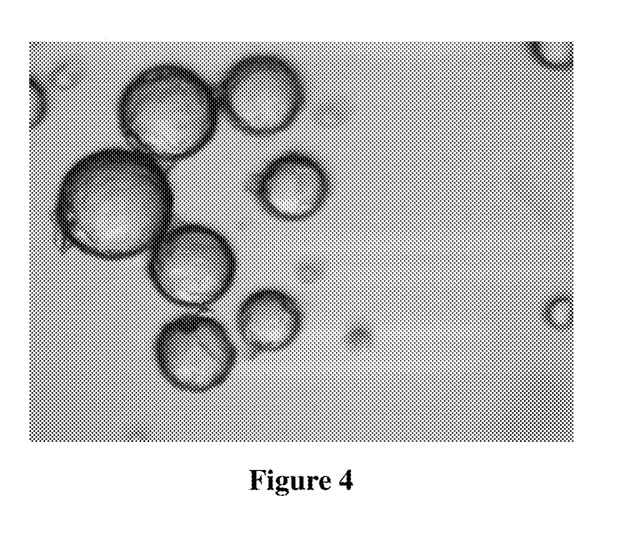
FIG. 4 shows light microscopic picture of large particles after EtO sterilization at 50° C. in matrix according to composition 1 in Table 1.
Figure 5:
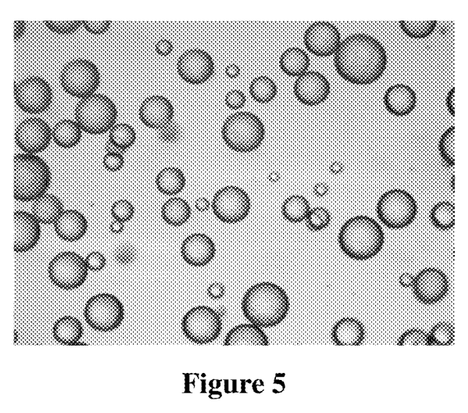
FIG. 5 shows light microscopic picture of large particles before EtO sterilization in matrix according to Composition 1 in Table 1.

Surprisingly, when matrix based microparticles are subject to EtO sterilization at 37° C., the particles retain their shape and size and can be reconstituted into a uniform and stable suspension by adding just de-ionized water or normal saline (0.9% solution of sodium chloride in water). See FIG. 3 which corresponds to composition 1. The inventive matrix compositions also produced a stable formulation even after sterilization at 50° C. as shown in FIG. 4 which corresponds to composition 5. For comparative purposes, see FIG. 5 which shows microparticles in the matrix without sterilization. Therefore, it is clear that the solid and porous matrix constitutes a composition that allows temperature sensitive microparticles to be sterilized at temperature as high as 50° C.

Example 7

Testing for Sterility

Twenty vials from two different lots were subject to testing for sterility using the United States Pharmacopeia (USP) method USP<71>. The results indicated that all the tested samples passed the test for sterility, indicating that the method of sterilization is successful.

What is claimed is:

1. A method of sterilizing polymer microparticles, comprising:
   (a) providing an aqueous solution having a viscosity of from about 100 to about 4,000 centipoise and containing a viscosity inducing polymer, a stabilizer and optionally a wetting agent so that an aqueous dispersion is formed;
   (b) lyophilizing the aqueous dispersion of step a) to produce a porous polymer matrix in which the polymer microparticles are substantially dispersed; and
   (c) exposing the porous polymer matrix containing the polymer microparticles substantially dispersed therein to a sterilizing gas at a temperature of 50° C. or lower and under conditions sufficient to substantially sterilize the lyophilized porous matrix containing the polymer microparticles, wherein the sterilizing gas is ethylene oxide.

2. The method of claim 1, wherein the viscosity inducing polymer is water soluble.

3. The method of claim 2, wherein the water soluble, viscosity inducing polymer is a cellulose derivative.

4. The method of claim 3, wherein the cellulose derivative is carboxy methylcellulose or the sodium salt of carboxy methylcellulose.

5. The method of claim 1, wherein the stabilizer is a polyhydric sugar or glycine.

6. The method of claim 5, wherein the polyhydric sugar is selected from the group consisting of mannitol, sucrose, glucose, trehlose and mixtures thereof.

7. The method of claim 1 wherein the wetting agent is selected from the group consisting of polymeric and non-polymeric surfactants.

8. The method of claim 7, wherein the wetting agent is polyvinyl pyrrolidone (PVP) or polyvinyl alcohol (PVA).

9. The method of claim 1, wherein the polymer microparticles have a cross-sectional diameter ranging of up to about 200 micrometers.

10. The method of claim 1, wherein the polymer microparticles have a cross-sectional diameter ranging from about 20 micrometers to about 150 micrometers.

11. The method of claim 1, wherein the viscosity of the aqueous solution prior to the polymer microparticles being dispersed therein is from about 100 to about 4,000 centipoise.

12. The method of claim 11, wherein the viscosity of the aqueous solution prior to the polymer microparticles being dispersed therein is from about 100 to about 2000 centipoise.

13. The method of claim 1 wherein the concentration of the polymer microparticles in the aqueous dispersion formed as a result of step a) is from about 10 to about 500 milligrams per milliliter.

14. The method of claim 13 wherein the concentration of the polymer microparticles is from about 10 to about 200 milligrams per milliliter.

15. The method of claim 1, wherein the aqueous solution in step a) prior to addition of the polymer microparticles comprises:
   i) from about 0.1 to about 2.0% w/w water soluble, viscosity inducing polymer;
   ii) from about 5 to about 15% w/w stabilizer; and
   iii) from about 0.1 to about 0.3% w/w wetting agent.

16. The method of claim 15, wherein the water soluble viscosity inducing polymer is NaCMC, the stabilizer is mannitol; and the wetting agent is polyvinylpyrrolidone (PVP).

17. The method of claim 1, wherein the sterilizing is carried out at a temperature of from about 20 to 50° C.

18. The method of claim 1, wherein the sterilizing is carried out at a temperature of ≤about 37° C.

19. The method of claim 1, wherein the pH of the aqueous suspension is from about 4.0 to about 8.0.

20. The method of claim 19, wherein pH of the aqueous suspension is from about 6.0 to about 7.5.

21. The method of claim 1, wherein the concentration of the viscosity inducing polymer in the aqueous suspension is from about 0.1 to about 2 percent on w/v basis prior to addition of the microparticles.

22. The method of claim 21, wherein the concentration of the viscosity inducing polymer is from about 0.5 to about 1 percent on w/v basis prior to addition of the microparticles.

23. The method of claim 1, wherein the volume of the lyophilized porous polymer matrix containing the polymer microparticles is 80% to 100% of the volume of the aqueous dispersion prior to the lyophilizing step.

24. The method of claim 1, further comprising suspending the sterilized lyophilized porous matrix containing the polymer microparticles in a solvent.

25. The method of claim 24, wherein the solvent is water.

26. The method of claim 24, wherein the water further comprises a salt or a sugar.

27. The method of claim 26, wherein the salt is sodium chloride and the sugar is glucose.

28. The method of claim 1, wherein the polymer microparticles are biodegradable.

29. The method of claim 1, wherein the polymer microparticles of step a) comprise a polylactic co-glycolic acid copolymer.

30. The method of claim 28, wherein the polymer microparticles further comprise an active medicament.

31. The method of claim 1, wherein the sterilizing is carried out with the wetting agent at a temperature of greater than about 45° C. and up to 50° C.

* * * * *